US005707736A

United States Patent [19]

Levy et al.

[11] Patent Number: 5,707,736
[45] Date of Patent: Jan. 13, 1998

[54] PRODUCTS HAVING ANTI-MICROBIAL ACTIVITY

[75] Inventors: David Levy, Migdal HaEmek; Hilda Guttmann, Jerusalem; Itzhak Kahane, Har Adar, all of Israel

[73] Assignees: Sion Texo Medic Ltd.; Yissum Research Development Co. of Hebrew Univ. of Jerusalem; Israel Fiber Institute, all of Jerusalem, Israel

[21] Appl. No.: 461,852

[22] Filed: Jun. 5, 1995

Related U.S. Application Data

[63] Continuation-in-part of Ser. No. 159,779, Dec. 3, 1993, abandoned, which is a continuation of Ser. No. 862,432, Apr. 2, 1992, abandoned.

[30] Foreign Application Priority Data

Apr. 4, 1991 [IL] Israel .................................. 97771

[51] Int. Cl.$^6$ .................................. D02G 3/00
[52] U.S. Cl. .................. 428/375; 428/372; 428/364; 428/393; 428/394; 428/395; 428/907; 442/59; 442/123; 442/152; 442/164; 442/165
[58] Field of Search ...................... 428/224, 253, 428/296, 288, 289, 364, 372, 393, 394, 395, 907, 375; 424/405, 403, 413, 407, 409, 443, 445, 447, 446, 404

[56] References Cited

U.S. PATENT DOCUMENTS

| 3,925,543 | 12/1975 | Donohue | 424/52 |
|---|---|---|---|
| 4,035,146 | 7/1977 | Brenner et al. | 8/115.6 |
| 4,062,793 | 12/1977 | Schödel | 252/99 |
| 4,122,158 | 10/1978 | Schmitt | 424/27 |
| 4,172,841 | 10/1979 | Danna et al. | 106/15.05 |
| 4,310,509 | 1/1982 | Berglund et al. | 424/28 |
| 5,069,907 | 12/1991 | Mixon et al. | 424/404 |
| 5,091,102 | 2/1992 | Sheridan | 424/404 |
| 5,104,660 | 4/1992 | Chuapil et al. | 425/445 |
| 5,116,620 | 5/1992 | Chuapil et al. | 425/445 |
| 5,152,996 | 10/1992 | Corey et al. | 424/443 |
| 5,156,843 | 10/1992 | Leong et al. | 424/411 |
| 5,487,896 | 1/1996 | Modak et al. | 424/404 |
| 5,576,006 | 11/1996 | Smith | 424/404 |

Primary Examiner—Patrick Ryan
Assistant Examiner—J. M. Gray
Attorney, Agent, or Firm—Hazel & Thomas

[57] ABSTRACT

The invention provides a dry, disposable, polymeric product having sustained-release anti-microbial activity, the product consisting essentially of a polymeric material selected from the group consisting of fibers, fabrics, sheets, films and other stable woven, non-woven and knitted materials prepared from natural, man-made and synthetic polymers and an amine salt anti-microbial agent, the anti-microbial agent being incorporated in the polymeric material without an intermediary adhesive, carrier or linking agent and being releasable therefrom in anti-microbially effective amounts for a period of at least three days upon the product being brought into contact with a moist surface.

14 Claims, No Drawings

PRODUCTS HAVING ANTI-MICROBIAL ACTIVITY

CROSS-REFERENCE TO RELATED APPLICATIONS

The present application is a continuation-in-part of U.S. patent application No. 08/159,779, filed Dec. 2, 1993, now abandoned, which in turn is a continuation of U.S. patent application No. 07/862,432, filed Apr. 2, 1992, now abandoned.

BACKGROUND OF THE INVENTION

The present invention relates to a dry, disposable, polymeric material having sustained-release, anti-microbial activity.

Numerous pathogens are present on the human skin. In general, and specifically in a hospital environment, it is desired that the growth of disease-producing microorganisms be inhibited and preferably that they be destroyed, so as to control patient infection and encourage wound healing. As a result, the application to the skin surface of topical, bactericidally active agents has become a standard part of the aseptic hospital technique.

DESCRIPTION OF THE PRIOR ART

The topical applications of broad-spectrum antimicrobials have been in the form of preoperative skin preparations, surgical scrub tissues as described, e.g., in U.S. Pat. No. 4,045,365, washes, wound cleansers, lotions, and ointments. In some instances, such a delivery is effective to the particular purpose for a limited period of time. Microorganisms that may have survived the initial application of the antimicrobial agent act as seeds, in some instances causing the pathogen population to rise to its initial level. Continuous application of an antimicrobial agent to the site is a means of inhibiting such an increase.

While numerous biologically active agents have been incorporated into adhesive layers on a substrate to provide a continuous application to the body of the agent, there has been no incorporation of a broad-spectrum antimicrobial into an adhesive layer which has been characterized by stability and unaltered activity of said antimicrobial. Examples of various agents that have been incorporated into adhesives are found in U.S. Pat. No. 2,137,169, in which phenol, thymol, methanol, etc., are added to a starch adhesive; U.S. Pat. No. 3,249,109, in which benzocaine was added to a tacky gelatin; U.S. Pat. No. 3,632,740, in which a corticosteroid is added to an adhesive; U.S. Pat. No. 3,734,097, in which a microencapsulated, anti-neoplastic agent is added to an adhesive; U.S. Pat. No. 4,073,291, in which Tretinoin is added to an adhesive; U.S. Pat. No. 3,769,071, in which 5-fluorouracil is incorporated into an adhesive; and U.S. Pat. No. 3,896,789, in which retinoic acid is incorporated into a pressure-sensitive adhesive tape.

U.S. Pat. No. 4,310,509 teaches and claims a pressure-sensitive adhesive composition which releases an antiseptically active, broad-spectrum antimicrobial when placed in contact with skin, comprising an antiseptically active amount of a broad spectrum antimicrobial agent and a dermatologically acceptable, room temperature tacky, pressure-sensitive adhesive which is chemically compatible with said broad-spectrum antimicrobial, said broad-spectrum antimicrobial agent being homogeneously and stably dispersed in said pressure-sensitive adhesive.

Similarly, U.S. Pat. No. 4,460,369 teaches and claims an adhesive, bacteria-proof wound dressing which, in use, consists essentially of a polyurethane sheet material which is 40 microns or less in thickness, having upon one surface a continuous layer of adhesive comprising a polyvinyl ether adhesive, or an acrylic adhesive up to 75 microns in thickness, which adhesive has incorporated in it, in uniform known amount per unit area, a solid antibacterial material in a finely divided form, in an amount of from 1–25% by weight of the adhesive, so that the dressing is liquid-impervious but has high moisture vapor permeability and releases the antibacterial material in an amount sufficient to kill bacteria in the wound and in the surrounding covered skin area.

U.S. Pat. No. 4,035,146 teaches the binding of antimicrobial compounds to a hydroxyl substrate using a cyanuric chloride linking agent; U.S. Pat. No. 4,122,158 teaches a method of treating a burn on an animal by administering a contact composition comprising a hydrophobic, bioerodible polymer containing a therapeutic agent wherein said polymer bioerodes over time, releasing said therapeutic agent.

SUMMARY OF THE INVENTION

With the above state of the art in mind, it is an object of the present invention to prepare antimicrobial, dry, disposable materials which are substantially free of adhesives, carriers, linking agents and other foreign elements which might interfere with the prolonged action of the antimicrobial agent.

More specifically, according to the present invention, there is now provided a dry, disposable, polymeric product having sustained-release antimicrobial activity, said product consisting essentially of natural polymers, man-made polymers and mixtures thereof in the form of fibers, yarns, woven, non-woven and knitted fabrics, sheets and films; and an amine salt antimicrobial agent; said antimicrobial agent being held by said polymeric material without an intermediary adhesive, carrier, or linking agent, and being releasable therefrom upon said product being brought into contact with a moist surface, in antimicrobial amounts effective for a period of at least three days.

In particular, the present invention provides a group of dry, disposable, medical dressings or supports produced from only two components: a polymeric material and an amine salt antimicrobial agent having a sustained-release activity towards *S. aureus*, *S. epidermidis*, and *E. coli* for a period of at least five days after contact with a moist or wet surface. A fully effective sustained-release activity lasts even for periods beyond twenty days, as exemplified hereinbelow.

The sustained-release activity of the products of the present invention is stable and fully effective (100%), working both after being treated at 134° C. for 15 minutes in a steam autoclave, and at room temperature without such treatment.

Thus, the term "stable" as used herein is intended to denote that the materials of the present invention retain their bioactivity even after heating.

The shelf life of wrapped products according to the present invention was tested over a period of three years. The antimicrobial slow-release activity of these products, when tested after such exposure, was 100% effective.

The materials envisioned for use in the present invention and to which the amine salt antimicrobial agents have been successfully directly bound, without the need for adhesives, linking agents, or other carriers, are natural polymers such as cotton, man-made polymers such as viscose rayon, cellulose triacetate, polypropylene, polyethylene and nylon and blends thereof.

Said antimicrobial agent can be any suitable broad spectrum amine salt antimicrobial, such as benzyl dimethyl, hexocyl ammonium chloride, benzylalkonium chloride, cetyl pyridinium chloride (monohydrate), chlorohexidine hydrochloride, chlorohexidine gluconate, septabididecyl dimethyl ammonium bromide (carbamide clatharate).

In preferred embodiments of the present invention, said antimicrobial agent is a chlorohexidine, and provides sustained-release activity against *Staphylococcus aureus* for at least eleven days, and even for periods beyond twenty days, as exemplified hereinbelow. In this context, it is worth mentioning that chlorohexidine (CHX) in aqueous solution was found to completely inactivate (100%), in 15 seconds, all human immunodeficiency virus type I, as reported in "Recommendation for Prevention of HIV Transmission in Health Care Settings: Morbidity and Mortality Report," *CDC Report*, Vol. 36, pp. 987–999 (1987). Such findings add to the known data of the broad range of antimicrobial activity of chlorohexidine, as reported, e.g., in J. F. Gardner and K. G. Gray, "Chlorohexidine," in *Disinfection, Sterilization and Prevention*, S. S. Block, Ed., Lea & Febiger, Philadelphia, Pa., U.S.A. (1983).

While the products of the present invention might appear, in hindsight, to be both simple and obvious, the opposite in fact is true. Today, there is no dry, disposable product having sustained-release, antimicrobial activity for a period of at least three days upon being brought into contact with a moist or wet surface. Furthermore, no one either taught or suggested a simple, two-component polymeric product consisting essentially of a polymeric material and an antimicrobial agent as defined herein, having the unexpectedly superior properties which are exemplified hereinbelow.

Thus, e.g., as mentioned above, U.S. Pat. No. 4,035,146 to Brenner et al. teaches the essential presence of a cyanuric chloric linking group. It should therefore be noted that said U.S. patent constitutes a teaching of the essential use of a linking agent which is quite reactive. Furthermore, this agent, which irritates the skin, eyes and respiratory system, has an $LD_{50}$ of 18 mg/kg and, when free, can decompose to emit cyanide.

U.S. Pat. No. 4,122,158 to Schmitt, also mentioned hereinabove, teaches the use of a bioerodible polymer having an active ingredient incorporated therein, said polymer and active ingredient being in turn contained in an absorbent carrier, and said agent being released with the erosion of the polymer (column 2, lines 25–27). In contradistinction thereto, the present invention does not include an intermediary, erodible polymer.

British Patent Application No. 2,109,237 similarly teaches a matrix material having a water-soluble particulate material incorporated therein, said particulate material preferably including a water-soluble glass, and said particulate material incorporated therein an active material. In contradistinction thereto, the present invention does not involve an intermediary, particulate, water-soluble material.

U.S. Pat. No. 5,156,843 to Leang et al. also similarly teaches a functional substance retained in the pores of microscopic porous particles, which porous particles are in turn impregnated into a fabric material. In contradistinction thereto, the present invention does not involve intermediary, microscopic porous particles.

Thus, Brenner '146, Schmitt '158, the British application, and Leang et al. '843 all teach a three-component system, involving the essential presence of a third component which is not required in the novel products of the present invention. It is clear that the complexity of preparing multi-component systems, as opposed to the simplicity of preparing a two-component system, and the disadvantage of having additional components present in such a system, prove that the prior art simply did not contemplate and, in fact, taught away from, the two-component system of the present invention.

The system of the present invention is also characterized by an unexpected superiority over the known prior art three-component systems. Thus, e.g., according to Brenner '146, the antimicrobial agents disclosed therein have an effective sustained-release for only 18 hours. In Barnes '256, the antimicrobial agents have an effective sustained-release for only 24 hours; the sustained-release agents of Schmitt '158 are effective for only 18 hours. None of these references either teaches or suggests a dry, disposable polymeric product having sustained-release, anti-microbial activity of at least three days, let alone a product having sustained release for over eleven days, as demonstrated hereinbelow in Examples 9 and 10.

The products of the present invention are produced as follows: the polymeric materials are brought into contact with a solution of the antimicrobial agent by immersion, spraying or coating, etc; the solvent is separated from the treated polymeric material by soaking, evaporation, or centrifugation, etc., and the polymeric materials are then dried by utilizing forced hot air, oven drying, air at room temperature, microwave drying, or the use of heated drying drums, vacuum chambers, etc.

For example, the fabric is immersed in a tub containing a diluted antimicrobial agent at room temperature. In a continuous process, the fabric is partially dried by being pressed with a padder. Drying is done by a dryer, i.e., a hot air blowing chamber or a hot drum chamber, heated up to 120° C. The speed of the continuous process is synchronized, and a winding machine then winds the processed fabric. The products are used as dressings or supports, to minimize the level of microbial contamination or to prevent the exposure of the injured site to additional microorganisms.

DETAILED DESCRIPTION OF TIFF, PREFERRED EMBODIMENTS

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A matrix made of cotton gauze 75 mm wide was soaked in 0.5% chlorohexidine gluconate (CHXG) aqueous solution at 25° C. and dried by forced hot air at 60° C. in a continuous process. The antimicrobial activity of the product was tested on lawns of several bacteria: *Staphylococcus aureus* (SA), *S. epidermidis* (SE), *Escherichia coli* (EC) and *Pseudonomas aeruginosa* (PA), inoculated on agar plates, by placing a sample of about 2 cm² on the surface of the plate, and measurement of the inhibition zone after growth of the bacterial for 18 hours at 37° C. After 24 hours, the sample was passed sequentially to another inoculated agar plate and the inhibition zone measured. This daily transfer procedure continued up to the loss of growth-inhibiting activity. The results are summarized below in Table 1.

The data set forth in the Tables herein is presented as follows:

a=no inhibition b=partial growth inhibition under matrix c=total growth inhibition under matrix d=growth inhibition beyond the matrix, but at less than 1 mm E x-y=growth inhibition in mm;
 x=minimum distance;
 y=maxxmum distance.

TABLE 1

MICROORGANISM GROWTH INHIBITION

| Transfer No | Hr. | SA | SE | EC | PA |
|---|---|---|---|---|---|
| 1 | 1 | E 4–5 | E4–5 | E4–5 | c |
| 2 | 42 | E 4–5 | E 1–2 | E 2–4 | a |
| 3 | 90 | E 1–2 | a | c | |

EXAMPLE 2

A matrix made of stretch gauze fabric consisting of nylon, viscose rayon and medically bleached cotton was soaked in 2% chlorohexidine gluconate aqueous solution at 25° C. and dried by forced hot air at 60° C. in a continuous process. When tested for efficacy against SA, growth of the bacteria was inhibited for 9 passages, made sequentially during a period of 29 days.

EXAMPLE 3

Paper Products

Filter paper strips, made of ordinary filter paper, or of Whatman #1 and #4 (Whatman Ltd.), were exposed to chlorohexidine gluconate solutions and were dried under the aforementioned conditions. Their antimicrobial activity was assessed as described in Example 1. The results are given below in Table 2.

TABLE 2

| Filter Paper | Antimicrobial Agent Conc. % | Microorganism Growth Inhibition (mm) | | | |
|---|---|---|---|---|---|
| | | SA | SE | EC | P |
| Regular | 0 | 0 | 0 | 0 | 0 |
| | 1 | E 5–6 | E 3–4 | E 4–5 | E 0–1 |
| | 5 | E 5–6 | E 4–5 | E 4–5 | E 2–3 |
| Whatman #1 | 0 | 0 | 0 | 0 | 0 |
| | 1 | E 4–5 | E 4–5 | E 4–5 | E 1–1 |
| | 5 | E 5–6 | E 4–5 | E 4–5 | E 2–3 |
| Whatman #4 | 0 | 0 | 0 | 0 | 0 |
| | 1 | E 5–6 | E 3–4 | E 4–5 | E 1–2 |
| | 5 | E 5–6 | E 4–5 | E 4–6 | E 2–3 |

EXAMPLE 4

Yarns

Yarns made of cotton, viscose, and nylon were soaked in aqueous solutions of chlorohexidine hydrochloride (CHXH) or chlorohexidine gluconate (CHXG), dried, and their antimicrobial activity tested. The results obtained with yarns treated with chlorohexidine hydrochloride (0.1%) are presented in Table 3.

TABLE 3

| MATRIX | GROWTH INHIBITION OF SA | |
|---|---|---|
| | 24 hour | 144 hour |
| Viscose | E 3 | E 3 |
| Cotton | E 1–2 | E 1–2 |
| Nylon | E 1 | only under the yarn |

EXAMPLE 5

Polymers

Cellulose triacetate, polypropylene, polyethylene and nylon were treated as above with chlorohexidine hydrochloride 0.1% or chlorohexidine gluconate 1.0%, and their antimicrobial activity was tested. The results are summarized in Table 4.

TABLE 4

| Matrix | Antimicrobial Agent | Growth Inhibition | | | |
|---|---|---|---|---|---|
| | | SA | SE | EC | PA |
| Cellulose triacetate | CHXH | E 5–6 | E 3–4 | E 2–4 | E 1–2 |
| | CHXG | E 4–5 | E 4 | E 3–4 | E 1 |
| Polypropylene | CHXH | E 2–4 | E 1–2 | E 1–3 | a |
| | CHXG | E 2–5 | E 2–3 | E 2–4 | a |
| Polyethylene | CHXH | E 3–4 | E 2 | E 1–3 | a |
| | CHXG | E 3–5 | E 3 | E 2–3 | E 1 |
| Nylon | CHXH | E 3–4 | E 2–3 | E 2–3 | a |
| | CHXG | E 3–5 | E 2–3 | E 2–4 | d |

EXAMPLE 6

Non-Woven Matrix

A non-woven matrix, made of polyethylene, viscose and cotton (Sion, Israel), used as pads for nursing mothers to protect the nipples, was treated as above with various chlorohexidine gluconate concentrations. Their antimicrobial activity is summarized in Table 5.

TABLE 5

| CHXG Concentration (%) | MICROORGANISM GROWTH INHIBITION | | | |
|---|---|---|---|---|
| | SA | SE | EC | PA |
| 2 | E 5–7 | E 3–5 | E 2–3 | d |
| 5 | E 4–5 | E 4–5 | E 3–4 | E 1–2 |

EXAMPLE 7

Dressing, treated as above in Example 1, but with 2% chlorohexidine gluconate, was incubated for 30 days at 55° C. and the antimicrobial activity was compared with that of a dressing incubated at room temperature. FIG. 1 shows the antimicrobial activity tested against *S. aureus* (A); *S. epidermidis* (B); *E. coli* (C), and *P. aeruginosa* (D), with relation to a control non-treated dressing (1); yarn (2); a treated dressing stored at room temperature (3); yarn from a treated dressing stored at 55° C. (4); and a treated dressing stored at 55° C. (5).

As is seen from the zones of inhibition in FIG. 1, dressings and the yarns from which they are made, stored at 55° C. for 30 days, retain antimicrobial activity similar to that of those stored at room temperature.

EXAMPLE 8

Spill of Contaminated Body Fluid

The product will be a dressing on a wound or a disposable lab coat, which will be exposed to a spill of the contaminated body fluid of an AIDS patient. Since chlorohexidine was demonstrated to be viricidal to HIV, and the site of the spill is an aqueous environment, the HIV reaching the matrix will most probably be killed and the chance for HIV infection of the bearer will be eliminated.

EXAMPLE 9

Radioactive chlorohexidine hydrochloride (CHXH) was prepared by the introduction of $^3$H tritium in the molecule. 0.01 g of a matrix made of cotton gauze was soaked for 30 minutes in radioactive chlorohexidine hydrochloride aqueous solution. The excess of CHXH solution was washed out from the matrix by rinsing the sample for 30 minutes in 20 ml L.B. medium. After that, the sample was washed three more times in 5 ml L.B. medium, for 1 minute each time.

To measure the release of CHXH from the sample, the following experiment was carried out:

The sample was placed in a 5 ml L.B. medium for 24 hours. The mount of CHXH released in the solution was measured by radioactivity measurement. The sample was placed in a new solution of 5 ml L.B. medium. The experiment was repeated 20 times. After 20 days, the experiment was stopped. The sustained-release was almost linear. During the 20 days, only about 4% of the amount of CHXH contained in the gauze after washing 3 times was released, indicating that the preponderance of CHXH was still retained in the gauze for further sustained release.

EXAMPLE 10

Wound Healing

Standard sized wounds were formed under anesthesia on the backs of guinea pigs (250–450 gr). The wounds were inoculated with S. aureus and covered with sterile pads. 55 minutes after inoculation, the wounds were treated by placing on them dressings made of either the fabric described in Example 1, but treated with 1% chlorohexidine gluconate, or an equally-sized gauze pad, wetted with "SAVIOR IC" or "POLYDAN" solution. After 11 days of daily replacement or the treated pads, or retention of the originally-applied single pad for 11 days, the wound areas were measured and the results were tabulated in Table 6, as set forth below.

TABLE 6

| | % Unhealed Wound Area (cm$^2$) | | | |
|---|---|---|---|---|
| | Daily Application | | Single Application | |
| | 4 Days | 10 Days | 4 Days | 10 Days |
| Pad wet with [Savior] "SAVIOR IC" | 0.80 | 0.40 | 1.07 | 0.60 |
| Matrix as prepared in Example 1 | 0.78 | 0.38 | 0.18 | 0.00 |
| Pad wet with [Polydin] "POLYDAN" | 0.78 | 0.40 | 0.60 | 0.40 |

As seen in Table 6, the best wound healing (statistically significant by T test) was in the group of animals treated with the matrix of Example 1 and by single application. The second best results were with the other group of animals treated with the matrix of Example 1 but replaced each day. These results clearly indicate the superiority and durability of sustained-release for a period of many days.

EXAMPLE 11

Matrix:

A standard woven matrix, manufactured by Shirley Development, Ltd., of England, consisting of six strips in which each strip is made of a different fiber, was utilized in this example. The following are the six various fibers in the woven matrix, and their identifying initials:

| CD | Secondary cellulose acetate (dicel) |
|---|---|
| C | Bleached unmercerized cotton |
| N | Nylon 6.6 |
| P | Polyester (terylene) |
| A | Acrylic (courtelle) |
| W | Worsted wool |

Procedure:

The matrix, consisting of the six above-mentioned fabrics, was soaked at 25° in a 2% chlorohexidine gluconate aqueous solution and dried by forced air at 100° C. in a continuous process.

The processed matrix was separated into six segments, each comprising one of the various fabrics. The antimicrobial activity of each segment was separately tested, as described above in Example 1. The results are given below in Table 7.

TABLE 7

Fabric Anti-Microbial Activity Test Results

| Fabric | Transfer No. | Microorganism Growth Inhibition | | | |
|---|---|---|---|---|---|
| | | SA | SE | EC | PA |
| CD | 1 | E 3–4 | E 2–3 | E 2–3 | E 0–1 |
| C | 1 | E 3–4 | E 2–3 | E 2–3 | E 0–1 |
| N | 1 | E 3–4 | E 2–3 | E 2–3 | a |
| P | 1 | E 3–4 | E 2–3 | E 2–3 | E 0–1 |
| A | 1 | E 3–4 | E 2–3 | E 2–3 | E 0–1 |
| W | 1 | E 3–4 | E 2–3 | E 2–3 | c |
| CD | 6 | E 2–3 | E 0–1 | E 1–2 | |
| C | 6 | E 2–3 | E 2–3 | E-2-3 | |
| N | 6 | a | a | a | |
| P | 6 | E 2–3 | E 2–3 | E 2–3 | |
| A | 6 | E 2–3 | E 2–3 | E 2–3 | |
| W | 6 | E 2–3 | E 2–3 | E 2–3 | |
| CD | 7 | E 2–3 | c | E 1–2 | |
| C | 7 | E 2–3 | c | E 2–3 | |
| N | 7 | a | a | a | |
| P | 7 | E 2–3 | c | E 2–3 | |
| A | 7 | E 2–3 | c | E 2–3 | |
| W | 7 | E 2–3 | c | E-2-3 | |
| After Washing: | | | | | |
| CD | 1 | E 2–3 | E 0–1 | E 1–2 | a |
| C | 1 | E 2–3 | E 1–2 | E 1–2 | E 0–1 |
| N | 1 | E 0–3 | a | E 0–1 | a |
| P | 1 | E 2–3 | a | E 0–1 | a |
| A | 1 | E 1–3 | a | E 0–1 | a |
| W | 1 | E 2–3 | E 0–1 | E-1-2 | a |

TABLE 7-continued

Fabric Anti-Microbial Activity Test Results

| Fabric Transfer No. | Microorganism Growth Inhibition | | | |
|---|---|---|---|---|
| | SA | SE | EC | PA |
| Stability - A Comparison: | | | | |
| C Unsterilized (treated with CHGH) | E 3–4 | E 2–3 | E 2–3 | E 0–1 |
| C Sterilized (autoclaved 134° C., 15 min) (treated with CHGH) | E 3–4 | E 2–3 | E 2–3 | c |

EXAMPLE 12

The procedure of Example 1 was repeated with the following amine salt antimicrobial agents, having the indicated identifying code numbers:

| 844 | Cetyl piridinium chloride |
|---|---|
| 846 | Bacitracin |
| 861 | Benzyl dimethyl hexocylammonium chloride |
| 868 | Septabicdidecyl dimethyl ammonium bromide |
| 836 | Chlorohexidine gluconate |

The antimicrobial activity of each of the products was tested on lawns of *Staphylococcus aureus* (SA). The results are summarized in Table 8 below:

TABLE 8

Amine Salt Anti-Microbial Activity Test Results

| | Antimicrobial Agent | Growth Inhibition SA |
|---|---|---|
| Day 1: | 844 | E 3–4 |
| | 846 | E 4–6 |
| | 861 | E 3–5 |
| | 868 | E 5–6 |
| | 836 | E 4–5 |
| Day 2: | 844 | E 5–6 |
| | 846 | E 1–3 |
| | 861 | E 3–4 |
| | 868 | E 5–6 |
| | 836 | E 3–4 |
| Day 3: | 844 | E 3–4 |
| | 846 | E b |
| | 861 | E 3–4 |
| | 868 | E 4–5 |
| | 836 | E 2–3 |
| Day 4: | 844 | B 2–4 |
| | 846 | E b |
| | 861 | E 2–3 |
| | 868 | E 3–4 |
| | 836 | E 2–3 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A dry, disposable polymeric anti-microbial-applying product having sustained-release anti-microbial activity, said product consisting essentially of:

a polymeric material selected from the group consisting of natural polymers, man-made-polymers and mixtures thereof in the form of fibers, yarns, woven, non-woven and knitted fabrics, sheets and films; and a water soluble amine salt anti-microbial agent, wherein said anti-microbial agent is releasably impregnated into said polymer material, coated on said polymeric material or a combination thereof without an intermediary adhesive or linking agent, and said anti-microbial agent is releasable from said polymeric material in anti-microbially effective amounts for a period of at least three days upon said anti-microbial product being brought into contact with a moist surface.

2. A dry, disposable, polymeric anti-microbial-applying product according to claim 1, wherein said water soluble amine salt anti-microbial agent is selected from the group consisting of chlorohexidine gluconate, chlorohexidine hydrochloride, benzyl dimethyl hexocylammonium chloride, benzylalkonium chloride, cetyl pyridinium chloride (monohydrate), and septabicdidecyl dimethyl ammonium bromide (carbamide clatharate).

3. A dry, disposable, polymeric anti-microbial-applying product according to claim 1, wherein said salt anti-microbial agent is directly impregnated into said polymeric material.

4. A dry, disposable, polymeric anti-microbial-applying product according to claim 1, wherein said anti-microbial agent is chlorohexidine hydrochloride.

5. A dry, disposable, polymeric anti-microbial-applying product according to claim 1, wherein said anti-microbial agent is chlorohexidine gluconate.

6. The dry, disposable, polymeric anti-microbial-applying product of claim 1, wherein the natural polymer is cotton.

7. The dry, disposable, polymeric anti-microbial-applying product of claim 1, wherein the man-made polymer is viscose.

8. The dry, disposable, polymeric anti-microbial-applying product of claim 1, wherein said polymeric material is in the form of a paper sheet.

9. The dry, disposable, polymeric anti-microbial-applying product of claim 1, wherein said polymeric material is in the form of a yarn.

10. The dry disposable, polymeric anti-microbial-applying product of claim 1, wherein said man-made polymer is selected from the group consisting of cellulose triacetate, polypropylene, polyethylene, nylon, and combinations thereof.

11. The dry, disposable polymeric anti-microbial-applying product of claim 1, wherein said polymeric material is in the form of a non-woven fabric made from polypropylene and cotton fibers.

12. A dry, disposable, polymeric anti-microbial-applying product according to claim 1, wherein said salt anti-microbial agent is coated on said polymeric material.

13. A dry, disposable, polymeric anti-microbial-applying product according to claim 1, wherein said salt antimicrobial agent is impregnated into and coated on said polymeric material.

14. A dry, disposable polymeric anti-microbial-applying product having sustained-release anti-microbial activity, said product consisting essentially of:

a polymeric material selected from the group consisting of natural polymers, man-made-polymers and mixtures thereof in the form of fibers, yarns, woven, non-woven and knitted fabrics, sheets and films; and a water-soluble amine salt anti-microbial agent, wherein said anti-microbial agent is releasably impregnated into said polymeric material, coated on said polymeric material or a combination thereof without an intermediary adhesive or linking agent, and whereby contact of said polymeric anti-microbial-applying product with a moist surface causes said polymeric material to release said anti-microbial agent in anti-microbially effective amounts for a period of at least three days.

* * * * *